(12) United States Patent
Ernst et al.

(10) Patent No.: US 10,202,319 B2
(45) Date of Patent: Feb. 12, 2019

(54) PROCESS FOR OLEFIN PRODUCTION BY METATHESIS AND REACTOR SYSTEM THEREFOR

(71) Applicant: Borealis AG, Vienna (AT)

(72) Inventors: Eberhard Ernst, Weissenfels (DE); Mariana Stoyanova, Berlin (DE); Evgeny Kondratenko, Rostock (DE); David Linke, Berlin (DE)

(73) Assignee: Borealis AG, Vienna (AT)

( * ) Notice: Subject to any disclaimer, the term of this patent is extended or adjusted under 35 U.S.C. 154(b) by 2 days.

(21) Appl. No.: 15/021,074

(22) PCT Filed: Sep. 11, 2014

(86) PCT No.: PCT/EP2014/069347
§ 371 (c)(1),
(2) Date: Mar. 10, 2016

(87) PCT Pub. No.: WO2015/036461
PCT Pub. Date: Mar. 19, 2015

(65) Prior Publication Data
US 2016/0229769 A1    Aug. 11, 2016

(30) Foreign Application Priority Data
Sep. 13, 2013  (EP) .................................. 13184369

(51) Int. Cl.
*C07C 6/04*      (2006.01)
*C07C 11/06*     (2006.01)
(Continued)

(52) U.S. Cl.
CPC  *C07C 6/04* (2013.01); *B01J 8/04* (2013.01); *C07C 5/2512* (2013.01); *B01J 23/10* (2013.01);
(Continued)

(58) Field of Classification Search
CPC ........................................................ C07C 6/04
See application file for complete search history.

(56) References Cited

U.S. PATENT DOCUMENTS 3,365,513 A    1/1968 Heckelsberg
3,546,313 A    12/1970 Banks
(Continued)

FOREIGN PATENT DOCUMENTS

CN    1520589 A    8/2004
EP    1854776 A1   11/2007
WO    2006052688 A2  5/2006

OTHER PUBLICATIONS

Banks et al., "New Developments and Concepts in Enhancing Activities of Heterogeneous Metathesis Catalysts", Journal of Molecular Catalysis, 1985, pp. 117-131, vol. 28.

*Primary Examiner* — Youngsel Jeong
(74) *Attorney, Agent, or Firm* — The Webb Law Firm

(57) ABSTRACT

The present invention relates to a process for obtaining an olefin by metathesis including the steps of i) feeding at least one stream with at least one olefin as starting material to at least one first reactor with at least one pre-bed having at least one compound selected from the group of alkaline earth oxides and ii) feeding the stream leaving the at least one first reactor to at least one second reactor downstream to the at least one first reactor including at least one main bed having a) at least one first catalyst component and b) at least one second catalyst component. The first and second catalyst are physically mixed with each other. The operational temperature of the at least one first reactor is lower than the operational temperature of the at least one second reactor.

17 Claims, 1 Drawing Sheet

● Standard configuration
◐ Dual bed (T(MgO)=250°C)
◑ Dual bed (T(MgO)=300°C)
◒ Dual bed (T(MgO)=400°C)

(51) Int. Cl.
*B01J 8/04* (2006.01)
*C07C 5/25* (2006.01)
*B01J 23/10* (2006.01)
*B01J 23/30* (2006.01)

(52) U.S. Cl.
CPC .......... *B01J 23/30* (2013.01); *B01J 2208/025* (2013.01); *B01J 2208/027* (2013.01); *C07C 2521/08* (2013.01); *C07C 2521/14* (2013.01); *C07C 2523/30* (2013.01); *Y02P 20/52* (2015.11)

(56) References Cited

U.S. PATENT DOCUMENTS

| | | | |
|---|---|---|---|
| 3,723,562 A | | 3/1973 | Heckelsberg |
| 3,865,751 A | | 2/1975 | Banks et al. |
| 3,915,897 A | | 10/1975 | Reusser et al. |
| 4,071,471 A | | 1/1978 | Banks et al. |
| 4,547,617 A | | 10/1985 | Welch |
| 4,575,575 A | | 3/1986 | Drake et al. |
| 5,120,894 A | * | 6/1992 | McCauley ............ C07C 5/2556 585/324 |
| 6,281,402 B1 | | 8/2001 | Coupard et al. |
| 6,875,901 B2 | * | 4/2005 | Gartside ............... C07C 5/2512 585/664 |
| 2004/0236572 A1 | | 11/2004 | Bietrix et al. |
| 2010/0056839 A1 | | 3/2010 | Ramachandran et al. |
| 2010/0167911 A1 | | 7/2010 | Shum |
| 2011/0263917 A1 | * | 10/2011 | Van Hal ................. C07C 5/417 585/322 |

\* cited by examiner

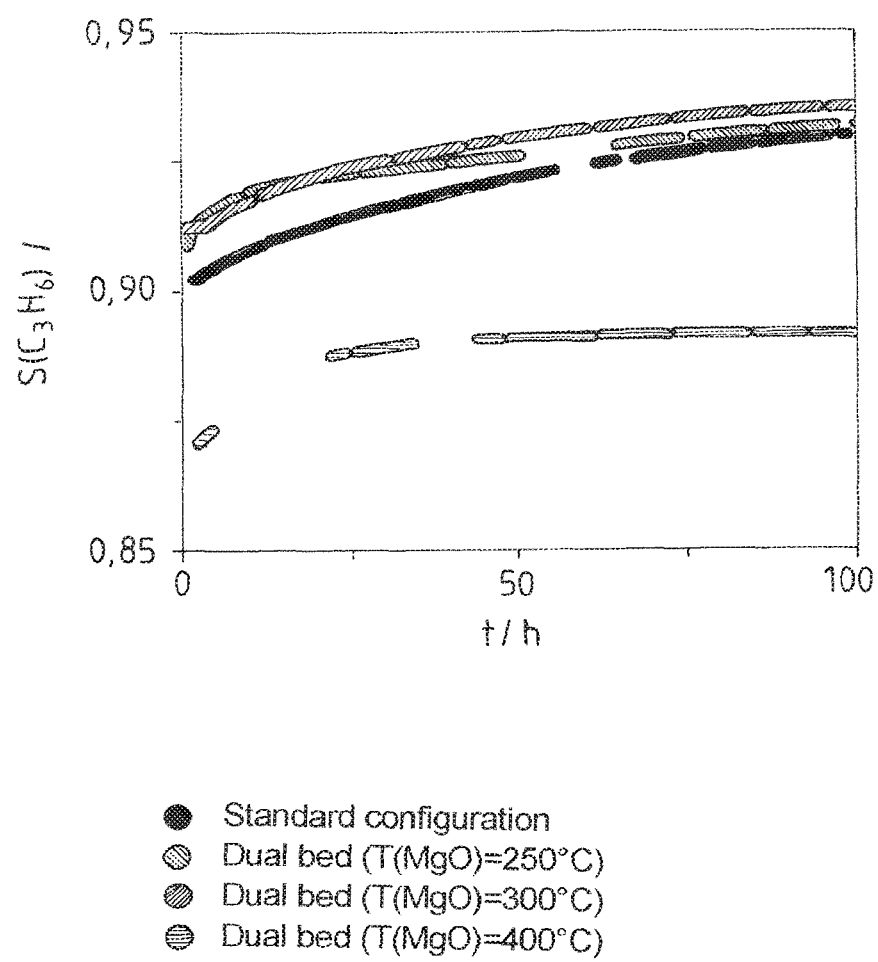

PROCESS FOR OLEFIN PRODUCTION BY METATHESIS AND REACTOR SYSTEM THEREFOR

CROSS-REFERENCE TO RELATED APPLICATIONS

This application is the United States national phase of International Application No. PCT/EP2014/069347 filed Sep. 11, 2014, and claims priority to European Patent Application No. 13184369.0 filed Sep. 13, 2013, the disclosures of which are hereby incorporated in their entirety by reference.

BACKGROUND OF THE INVENTION

Field of the Invention

The present invention relates to a process for obtaining an olefin and a reactor system.

DESCRIPTION OF RELATED ART

Butenes are the $C_4H_8$ mono-olefin isomers such as 1-butene, cis-2-butene, trans-2-butene and iso-butene (2-methylpropene). If it is not specifically mentioned, cis-2-butene, trans-2-butene are also called as 2-butene within the frame of the present invention. The sum of cis-2-butene, trans-2-butene, and 1-butene is denoted as n-butenes. Butenes are almost always commercially produced as by-products in a petroleum refinery by cracking processes or by catalytic ethene dimerisation. Butenes can be used for multiple purposes like in the manufacture of polymers and other chemicals like insecticides, antioxidants, adhesives, sealants or elastomers.

The use of n-butenes for the production of propene has gained industrial importance in the last decades. The synthesis of propene using n-butenes as starting material is based on the metathesis reaction. Hereby, 2-butene is converted in the presence of ethene to propene according to the following overall reaction scheme:

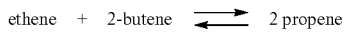

ethene + 2-butene ⇌ 2 propene

This reaction occurs typically in the presence of a catalyst comprising an oxide of metals of the group 6 or 7 of the periodic system of the elements (PSE). Typical active components of metathesis catalysts are tungsten oxide supported on silica (U.S. Pat. No. 3,365,513), rhenium oxides, or molybdenum oxides supported on alumina or silica alumina (U.S. Pat. No. 4,547,617; U.S. Pat. No. 6,281,402).

Various modifications and improvements of the known metathesis catalysts have been described. The physical mixing of the metathesis catalyst with an isomerisation catalyst for shifting the double bond in 1-butene to yield 2-butene has been proven to increase the overall production yield of propene (U.S. Pat. No. 3,865,751; U.S. Pat. No. 3,915,897; U.S. Pat. No. 4,575,575). Typical double bond isomerisation catalysts include basic metal oxides as for instance magnesium oxide (MgO) or calcium oxide (CaO), which can be admixed with the metathesis catalyst. A physical mixture of such basic oxide with a metathesis catalyst is called as main bed. The use of magnesium oxide (MgO) as a co-catalyst enables to operate at a reduced reaction temperature between 250° C. and 300° C. compared to approximately 400° C. as required for pure silica supported tungsten oxide ($WO_3/SiO_2$). The weight ratio of MgO to $WO_3/SiO_2$ in the main bed is in the range of 0.1-20. Magnesium oxide has the function to isomerise 1-butene to 2-butene since both olefins are present in technical feeds and to avoid the enrichment in the feed after recycling of non-converted n-butenes. It is important to highlight that magnesium oxide alone shows negligible metathesis activity.

Besides its ability to act as an isomerisation catalyst magnesium oxide has also been known for its ability to remove or destroy traces of contaminants from the olefin feed that are detrimental to metathesis catalysts, in particular when used as a "guard bed" (J. Mol. Cat. 1985, 28:117-131). Magnesium oxide can be for instance arranged on top of a composition comprising the metathesis catalyst and an isomerisation catalyst (US 2010/0056839 A1, US 2010/167911 A1). Here the optimal catalyst activation is combined with the guard pre-bed function to remove poisons and the isomerisation of 1-butene to 2-butene. When applying this approach a technical metathesis reactor is typically filled with a mixture of MgO and $WO_3/SiO_2$ and an additional bed of MgO pre-bed upstream of the main bed. The latter MgO bed or other catalyst beds located above (upstream) the main bed are called as pre-bed.

It is also known that both beds—pre-bed and main-bed—can be arranged in separate layers within the same reactor without losing the catalyst activity (J. Mol. Cat. 1985, 28: 117-131). Additionally, it is also described that pre-bed and main-bed can be operated at different temperatures. The highest catalyst activities were described if MgO pre-bed and catalyst main bed MgO—($WO_x$—$SiO_2$) mixture are used at similar temperatures. Thus, one may can conclude that both beds should be located in one reactor to achieve an optimal catalyst and reactor performance.

The on-purpose production of propene is the main target of the commercial metathesis technology. It is of general interest to improve the catalyst performance and especially propene selectivity and yield. Current commercial processes are using metathesis reactors where magnesium oxide pre-bed and the main-bed which is a physical mixture of magnesium oxide and silica supported tungsten oxide pellets are located in one reactor. The reactor is operated under adiabatic conditions (i.e. no heat transfer across the boundary between the thermodynamic system and the surroundings) which means that the reaction heat is taken up by the reaction mixture. The reaction is slightly exothermic. The temperature increase over the bed length is in the range of 4° C. to 10° C. For these reasons it is difficult to adjust a different temperature in the pre-bed without changing the reaction temperature in the main bed. As a consequence if olefin isomerisation occurring in the MgO pre-bed and metathesis reaction taking place in the main-bed cannot be performed at their individual optimal temperatures, i.e. the optimisation of the whole process in terms of propene production is problematic.

SUMMARY OF THE INVENTION

It is therefore an object of this invention to provide a process which allows for an optimisation of the olefin, in particular propene, production by independently optimising the temperature conditions of the process.

Accordingly, a process for obtaining an olefin by metathesis is provided comprising the steps of
  feeding at least one stream comprising at least one olefin as starting material to at least one first reactor with at least one pre-bed comprising at least one compound selected from the group of oxides of alkaline earth metals, wherein the at least one first reactor is operated at an operational temperature T1, and feeding the stream leaving the at least one first reactor to at least one second reactor downstream from the at least one first reactor comprising at least one main bed comprising a) at least one first catalyst component comprising a metathesis catalyst, and b) at least one second catalyst component comprising a catalyst for double bond isomerisation, whereby the first and second catalysts are physically mixed with each other, wherein the at least one second reactor is operated at an operational temperature T2. Thus, pre-bed and main-bed are arranged in each case in at least two different reactors spatially separated from each other. There is no direct physical contact between the pre-bed and main-bed.

The separated arrangement of pre-bed and main-bed in two different reactors allows for independent control and setting their temperatures that is detrimental for optimizing the catalytic performance of pre-bed and main-bed.

Thus, the present process is further characterized in that the operational temperature T1 of the at least one first reactor is in a range between 150° C. and 300° C. and the operational temperature T2 is in a range between 250° C. and 350° C. of the at least one second reactor.

In an embodiment the operational temperature T1 of the first reactor is at least 20°, preferably at least 40° C., most preferably at least 50°, outmost preferably at least 100° C. lower than the operational temperature T2 of the second reactor.

It has been surprisingly found that the temperature optimum for pre-bed and main-bed and thus the temperature optimum of the reactions taking place in the pre-bed and main-bed, respectively, differ from each other. It has also been found that the olefin selectivity (such as propene selectivity) can be increased without decreasing the conversion of starting olefins (such as 2-butene and ethene) if the first reactor with the pre-bed (isomerisation reactor) is operated for instance at 250° C. and the second reactor with the main bed (metathesis reactor) is operated for instance at 300° C. The increase in selectivity leads finally to a reduction of energy consumption in the following distillation unit and an increased plant capacity.

In a preferred embodiment of the present process the operational temperature T1 of the first reactor is in a range between 200° C. and 300° C., most preferably between 220° C. and 280° C., outmost preferably between 240° C. and 260° C., in particular at 250° C., and the operational temperature T2 of the second reactor is in a range between 270° C. and 330° C., most preferably between 290° C. and 310° C., mostly preferred at 300° C.

In an embodiment of the present process a stream containing a first olefin, in particular a C4-olefin such as butene, is fed to the first reactor with the pre-bed. The stream of the first olefin leaving the first reactor is then mixed with a second olefin, in particular ethene, and the mixture of the first and second olefin is subsequently fed to the second reactor with the main bed, where the actual metathesis reaction takes place. Thus, in case two olefins are used as starting material it is possible to pass only one of these olefins through the pre-bed, where for instance isomerisation of said olefin occurs. The second olefin is not passed through the first reactor with the pre-bed, but is rather admixed with the first olefin just before entering the second metathesis reactor. In a specific embodiment only n-butene is passed through the first reactor and is subsequently mixed with ethene after leaving the first reactor before entering the second reactor.

According to another preferred embodiment a stream comprising at least two olefins as starting materials for metathesis are fed into the first reactor with the pre-bed, i.e. first and second olefin are combined and fed as a mixture to the first reactor with the pre-bed and subsequently after leaving the first reactor are fed to the second reactor with the main bed. Thus, in this case first and second olefin are passed together through the first reactor. In a specific embodiment n-butene and ethene are fed together into the first and second reactor.

It is to be understood that it is also possible to feed two olefins into the first reactor, which are mixed with a third olefin after leaving the first reactor before entering the second rector. Another possibility is to feed one olefin, in particular 2-buten, into the first reactor and mixing the same with two further olefins after leaving the first reactor before entering the second reactor. Any suitable combinations are here possible.

In another embodiment of the process the pressure applied in the at least one first reactor and the at least one second reactor is between 1 to 50 bar, in particular 10 to 30 bar. It is in particular of an advantage if the pressure in the first reactor is equal to the pressure in the second reactor.

However, it is also conceivable and possible that the pressure in the first reactor with the pre-bed may be increased in respect to the pressure in the second reactor with the main bed. A higher pressure will extent the cycle time between two regeneration steps. The pressure in the first pre-bed reactor may be thus 50 bar, preferably 30 bar, most preferably 10 bar higher than in the second metathesis reactor.

In a further embodiment of the present process the mass ratio of the at least one pre-bed in the at least one first reactor and the at least one main bed in the at least one second reactor is between 1:10 and 3:1, preferably between 1:6 and 2:1, most preferably between 1:4 and 1:2.

In a further embodiment the metathesis catalyst in the main bed of the present invention comprises metal oxides from metals of group 6 and 7 of the PSE, in particular tungsten oxide, molybdenum oxide and/or a precursor thereof, which are the active components and are deposited on at least one inorganic carrier. The most preferred metal oxide is tungsten oxide.

Preferably, the at least one inorganic carrier is selected from a group comprising silica, alumina, silica-alumina or aluminium phosphate. The inorganic carrier can contain at least about 0.1 wt % and up to 40 wt % of the active components. Amounts between 1 to 30 wt % are preferred, whereby amounts between 2 to 15 wt % are mostly preferred.

The metathesis catalyst may further comprise at least one oxide of a metal of the group I of the PSE or a precursor thereof as for instance comprising oxides, hydroxides, carbonates, bicarbonates, nitrates, acetates of sodium or potassium or mixtures thereof. Especially preferred are the hydroxides of sodium and potassium. The amount of these promoting compounds can be between 0.01 and 10 wt %, preferably between 0.1 and 10 wt % with respect to the metathesis catalyst. The metathesis catalyst may be impregnated with said promoting compound.

The BET surface area of the metathesis catalyst is at least >10 m$^2$/g, preferably at least >50 m$^2$/g and mostly preferably at least ≥100 m$^2$/g.

The particle size of the metathesis catalyst depends on the reactor size. When applied as powder like for instance in lab size reactors, the typical particle size of the metathesis catalyst is between 0.3-0.7 mm. When used in larger reactors like for instance technical reactors the particle size is in the range between 1 and 10 mm, preferably between 1 and 8 mm, most preferably between 1 and 5 mm.

In another preferred embodiment said second catalyst component for double bound isomerisation of the main bed composition comprises Group 2 metal oxides, in particular magnesium oxide, calcium oxide, barium oxide, strontium oxide.

The isomerisation catalyst may also be activated for instance by heating in a flow stream of an oxygen-containing gas for about 1 to 30 hours at about 250° C. to 800° C. After calcination the isomerisation catalyst may be treated under reducing conditions as for instance with a reducing gas as hydrogen or carbon monoxide (U.S. Pat. No. 4,575,575; U.S. Pat. No. 3,546,313).

The main bed can then be prepared by admixture of the double bond isomerisation catalyst and the metathesis catalyst. The catalysts are preferably mixed in form of powders, pellets or extrudates.

The amount of the isomerisation catalyst is preferably in excess of the amount of the metathesis catalyst. However, the isomerisation catalyst can also be used in lower amounts. In an embodiment the main bed composition comprises the at least one isomerisation catalyst component and the at least one metathesis catalyst component in a ratio between 5:1 and 1:1, preferably in a ratio 4:1 and 2:1, most preferably in a ratio of 3:1. It is important to note here that the weight ratio of isomerisation catalyst to metathesis catalyst does not show any influence on the overall process conversion time and yield.

The activation of the main bed is preferably carried out by heating the reactor system in an oxygen containing inert gas, like for instance nitrogen and with a reducing gas, like carbon monoxide or hydrogen (U.S. Pat. No. 3,915,897; U.S. Pat. No. 3,365,513).

The catalyst activation is preferably carried out in multiple steps. The activation can be for instance carried out according to WO 2006/052688. Typically, at first the catalyst is being oxidized for 15 to 20 minutes at a temperature between 350 and 800° C. followed by reduction for 1 to 30 hours at a temperature between 350 and 400° C., for instance in the presence of hydrogen. Subsequently, a desorption step above 500° C. is required in order to remove adsorbed carbon dioxide and water.

In an especially preferred embodiment said pre-bed comprises an oxide selected from the group consisting of magnesium oxide, calcium oxide, strontium oxide, barium oxide or mixtures thereof. The oxides of the pre-bed such as magnesium oxide can be used for the purification of olefin streams. This purification is based on the removal of traces of moisture, carbon dioxide and other polar compounds by adsorption. These compounds act as poisons for the catalyst when entering the reactor. Said compounds are adsorbed on the catalyst (e.g. magnesium oxide) and form acidic centres which are the source for coke formation. Subsequently, the coke covers the active sites and the catalyst is deactivated. The result of this process is a deactivation reaction which is visible as decline of the yield/conversion curve over the reaction time on stream (tos). Thus, then using the present pre-bed the olefin streams are purified before entering the main bed. Besides purification an isomerisation reactions of the olefin fed to the pre-bed occurs as well, as previously described.

The average BET surface of the compounds used as pre-bed is at least >10 m$^2$/g, preferably at least >50 m$^2$/g and mostly preferably at least ≥100 m$^2$/g.

The particle size of the components of the pre-bed depends on the reactor size. When applied as powder like for instance in lab size reactors, the typical particle size of the metathesis catalyst is between 0.3-0.7 mm. When used in larger reactors like for instance technical reactors the particle size is in the range between 1 and 10 mm, preferably between 1 and 8 mm, most preferably between 1 and 5 mm.

Said pre-bed can be the same or can be different from the at least one double bond isomerisation catalyst in the main bed.

The metathesis reaction is preferably performed at a Weight Hourly Space Velocity (WHSV) in the range between 1 and 100 h$^{-1}$, preferably between 1 and 50 h$^{-1}$, more preferably between 1 and 10 h$^{-1}$ (the WHSV values are referring to the main bed and the fed 2-butene).

In an embodiment the one of the at least two olefins used as starting material comprises at least two carbon atoms, such as ethene, and the second of the at least two olefins used as starting material comprises at least four carbon atoms, such as a 2-butene. The mole ratio between said olefin comprising at least two carbon atoms and the olefin comprising at least four carbon atoms can be 1:20, preferably 1:10, mostly preferably 1:5 and most preferably 1:2.5.

The at least two olefins may be supplied to the first reactor as a mixed stream or in form of separated streams. When using 2-butene as starting material, the butene component may be supplied as cis- or trans-2-butene or mixtures thereof. A technical 2-butene stream may contain additional small amounts of n-butane, iso-butane, iso-butene, 1-butene. In some embodiments the mixed C4 stream is pre-treated to increase the 2-butene content in the feed for the metathesis reaction. If a crude C4 cut from an e.g. naphtha cracker is used compounds like 1,3-butadiene, allenes or acetylenes have to be removed by a selective hydrogenation step.

The olefin mixture is then contacted at first with the pre-bed in the first reactor, where an isomerisation reaction, in particular of 1-butene to 2-butene, takes place.

When entering the main bed comprising the metathesis catalyst and the isomerisation catalyst in the second reactor (2), further isomerisation and new olefin production (such as propene-production) by metathesis occur. Besides propene also other reaction products can be formed such as for example $C_5$-$C_6$ olefins.

The process may be carried out by contacting the olefins with the catalysts in the liquid phase or the gas phase depending on structure and molecular weight of the olefins used as starting material, the catalyst used and/or the reaction conditions applied such as pressure, temperatures etc. Diluents such as saturated aliphatic hydrocarbons, such as methane, ethane, propane, butane and/or inert gases like nitrogen or argon might be suitable. In any case, the presence of deactivating substances like water, carbon dioxide or oxygen should be avoided.

The metathesis catalyst is very sensitive to impurities in the feed stream. Such feed poisons are, for example, strong polar or protic compounds such as N—, O—, S— and halogen comprising compounds or carbon oxide derivatives. Typical examples are water, alcohols, ethers, ketones, aldehydes, acids, carbon dioxide, carbon monoxide, carbon oxide sulfide and the like. The consequences are reduced catalyst activity and shortened propene production cycle times. Therefore the feed stream must be purified by passing it through suitable adsorbents before feeding to the reactors.

It is also possible to conduct the reaction in the presence of hydrogen (EP 1854776 A1).

The effluent from the second reactor (metathesis reactor) can be sent to a separation system for separating the product(s) from unreacted feed components. For instance, the products of the separation system may include ethene, propene, $C_4$- and $C_5$-olefins. The propene separated from the reaction stream is characterised by a high purity. The ethene and $C_4$ olefins may be recycled back to the metathesis reactor or to a pre-treatment stage.

The present process is carried out in a reactor system comprising i) at least one first reactor with at least one pre-bed comprising at least one compound selected from the group oxides of alkaline earth metals, and ii) at least one second reactor comprising at least one main bed comprising a) at least one first catalyst component comprising a metathesis catalyst, and b) at least one second catalyst component comprising a catalyst for double bond isomerisation, whereby the first and second catalyst are physically mixed with each other. The at least one first reactor and the at least one second reactor are arranged sequentially to each other, with the former being located upstream of the latter.

The first and second reactors are preferably fixed-bed reactors. Basic types of catalytic fixed-bed reactors are the adiabatic fixed-bed reactor and the isothermal fixed-bed reactor. The adiabatic fixed-bed reactor is preferred for technical processes. Pre-bed and main-bed are usually provided in the fixed-bed reactor in form of random packings of powders, pellets or extrudates, for instance of catalytic pellets.

Typically the reactor is a packed fixed-bed reactor, which is widely used for gas solid reactions.

In an embodiment the at least one first reactor and the at least one second reactor have in each case a length to diameter ratio (l/d ratio) between 1 and 15, preferably between 1 and 10, most preferably between 1 and 5, even more preferably between 1.5 and 3.5.

However, it is also conceivable and possible that the first reactor (pre-bed reactor) and the second reactor (main bed reactor) are of different volumes. It is for instance of an advantage if the first reactor is of a smaller volume than the second reactor. The volume ratio (V/V) of first and second reactors may be 0.05-1.0, preferably 0.1-0.8, more preferably 0.2-0.5, most preferably 0.2-0.3.

In general the reactor construction and dimension of first and second reactors are determined by different process factors: the minimum diameter of the reactor should be at least 10 times larger than the particle diameter of the catalyst, the height of the catalyst bed should be at least 50 times larger than the particle diameter, the bulk density of the pre-bed and main bed components are of importance as well as the desired Weight Hourly Space Velocity.

The first and second reactors are connected by a suitable pipeline for transferring the olefin stream leaving the first reactor into the second reactor where the actual metathesis reaction takes place. The connecting pipeline should be as short as possible for avoiding any undesired side reactions. It is preferred if the connecting pipeline is temperature controlled and equipped with a trace heating. The temperature of the connecting pipeline is preferably in the same range as the operational temperature T2 of the second reactor. For instance the olefin stream leaving the first reactor may be heated in said pipeline to a temperature of about 300° C.

BRIEF DESCRIPTION OF THE DRAWINGS

The present invention is further explained in more detail by the means of the following examples with reference to the FIGURE. It shows:

FIGURE: a diagram illustrating the propylene selectivity in dependency on the time-on-stream in ethene-2-butene metathesis for a first embodiment of the process according to the invention.

DETAILED DESCRIPTION OF THE INVENTION

Example 1: Catalyst Preparation

The $WO_x/SiO_2$ catalyst was prepared according to U.S. Pat. No. 4,575,575, example 1, catalyst component C. Commercial magnesium oxide powder was used, which was pelletized and crushed to receive the necessary particle size of 0.3 to 0.7 mm.

Example 2: Standard Reactor Configuration, Comparative Example

A conventional metathesis reactor (2) was loaded with 600 mg of main bed (a physical mixture of MgO and $WO_3/SiO_2$ powder particles with a diameter of 0.3 to 0.7 mm in the mass ratio of 3:1) and with 150 mg of pure MgO (pre-bed) arranged upstream. The mass ratio between the pre-bed and main bed was 1 to 4. The reactor was operated at 300° C. The catalytic results are summarised in table 1.

Example 3: Dual Reactor Configuration, T (MgO Pre-Bed)=300° C.

The metathesis reactor (2) was loaded with 712 mg of main bed. Another separate reactor, the so-called pre-bed reactor (1) arranged upstream of reactor (2) contained 150 mg of pure MgO. Both reactors (1, 2) were operated at 300° C. The catalytic results are summarised in table 1.

Example 4: Dual Reactor Configuration T (MgO Pre-Bed)=250° C.

The metathesis reactor (2) was loaded with 712 mg of main bed and operated at 300° C. The amount of MgO pre-bed in the upstream pre-bed reactor (1) was 150 mg. Its temperature was 250° C. The catalytic results are summarised in table 1.

Example 5: Dual Reactor Configuration T (MgO Pre-Bed)=400° C.

The metathesis reactor (2) was loaded with 712 mg of main bed and operated at 300° C. The amount of MgO pre-bed in the upstream pre-bed reactor (1) was 150 mg. Its temperature was 400° C. The catalytic results are summarised in table 1.

TABLE 1

Reactor configuration, reaction conditions and selected catalytic results
(conversion of t-2-butene - X(t-2-C$_4$H$_8$), propene selectivity - S(C$_3$H$_6$) and propene yield -
Y(C$_3$H$_6$)) after 2, 50 and 100 hours on metathesis stream.

| Ex | Reactor | T$_1$/ °C. | T$_2$/ °C. | X(t-2-C$_4$H$_8$)/% 2 h | 50 h | 100 h | S(C$_3$H$_6$)/% 2 h | 50 h | 100 h | Y(C$_3$H$_6$)/% 2 h | 50 h | 100 h |
|---|---|---|---|---|---|---|---|---|---|---|---|---|
| 2 | Standard | 300 | 300 | 86.3 | 88.2 | 86.5 | 90.2 | 92.2 | 93.0 | 77.8 | 81.3 | 80.5 |
| 3 | Dual bed | 300 | 300 | 87.2 | 87.6 | 81.2 | 91.2 | 92.9 | 93.5 | 79.6 | 81.5 | 76.0 |
| 4 | Dual bed | 300 | 250 | 87.7 | 88.1 | 87.1 | 91.3 | 92.6 | 93.2 | 80.0 | 81.6 | 81.2 |
| 5 | Dual bed | 300 | 400 | 86.2 | 88.8 | 86.4 | 87.0 | 89.0 | 89.1 | 75.0 | 79.1 | 77.1 |

T$_1$ is the reaction temperature of MgO:(WO$_x$/SiO$_2$) = 3:1 main-bed metathesis reactor
T$_2$ is the reaction temperature of MgO pre-bed isomerisation reactor The conversion of t-2-C$_4$H$_8$ was calculated on the basis of its inlet and outlet mole fractions (equation 1). The product selectivity was calculated on a molar basis (equation 2). 1-C$_4$H$_8$ and cis-2-C$_4$H$_8$ were considered as reaction products. The propene yield is a product of the propene selectivity and the t-2-butene conversion (equation 3).

$$X_{t\text{-}2C_4H_8} = \left(1 - \frac{x^{outlet}_{t\text{-}2C_4H_8}}{x^{inlet}_{t\text{-}2C_4H_8}}\right) \times 100\% \quad (1)$$

where x is mole fraction of t-2-butene.

$$S_{C_3H_6} = \frac{n^{outlet}_{C_3H_6}}{n^{outlet}_{C_3H_6} + n^{outlet}_{1\text{-}C_4H_8} + n^{outlet}_{cis\text{-}2C_4H_8} + \Sigma n^{outlet}_{C_5} + \Sigma n^{outlet}_{C_6}} \times 100\% \quad (2)$$

where $n_i^{outlet}$ is number of moles of propylene, 1-butene, cis-2-buetene, pentenes (C$_5$) and hexenes (C$_6$) at the reactor outlet.

$$Y_{C_3H_6} = S_{C_3H_6} \times X_{t\text{-}2\text{-}C_4H_8} \times 100\% \quad (3),$$

where $S_{C_3H_6}$ is propene selectivity and $X_{t\text{-}2\text{-}C_4H_8}$ is conversion of t-2-butene calculated according to equations 1 and 2, respectively.

The examples in Table 1 as wells as in the diagram of the FIGURE clearly demonstrate that catalytic properties such as conversion, propene selectivity and yield can be improved if the metathesis process is carried out using MgO pre-bed and MgO—(WO$_x$—SiO$_2$) catalyst main bed in two separate reactors, which operate in a temperature range between 250 and 300° C.

The invention claimed is:

1. A process for obtaining propene by metathesis comprising the steps of
    feeding at least one stream comprising ethene and 2-butene, wherein 2-butene is supplied as a technical 2-butene stream containing 1 butene, as starting material to at least one first reactor with at least one pre-bed comprising at least one compound selected from the group consisting of alkaline earth metal oxides, wherein the at least one first reactor is operated at an operational temperature T1, and
    feeding at least one stream leaving the at least one first reactor to at least one second reactor downstream of and separate from the at least one first reactor comprising at least one main bed comprising
    a) at least one first catalyst component comprising a metathesis catalyst, and
    b) at least one second catalyst component comprising an isomerisation catalyst for double bond isomerisation, wherein the at least one first catalyst and the at least one second catalyst are physically mixed with each other,
    wherein the at least one second reactor is operated at an operational temperature T2,
    wherein
    the operational temperature T1 of the at least one first reactor is in a range between 150° C. and 280° C. and the operational temperature T2 of the at least one second reactor is in a range between 290° C. and 350° C., and
    wherein the operational temperature T1 of the at least one first reactor is at least 40° C. lower than the operational temperature T2 of the at least one second reactor.

2. The process according to claim 1, wherein the operational temperature T1 of the at least one first reactor is in a range between 200° C. and 280° C.

3. The process according to claim 1, wherein the operational temperature T2 of the at least one second reactor is in a range between 290° C. and 330° C.

4. The process according to claim 1, wherein a stream comprising one first olefin is fed to the at least one first reactor, is mixed with at least one third olefin after leaving the at least one first reactor forming a mixture of the effluent resulted from the at least one first reactor and the at least one third olefin which is subsequently fed to the at least one second reactor.

5. The process according to claim 1, wherein a stream comprising at least two olefins as starting materials for metathesis is fed into the at least one first reactor and subsequently after leaving the at least one first reactor is fed to the at least one second reactor.

6. The process according to claim 1, wherein a pressure in the at least one first reactor and the at least one second reactor is between 1 to 50 bar.

7. The process according to claim 1, wherein a pressure in the at least one first reactor is higher or equal to a pressure in the at least one second reactor.

8. The process according to claim 1, wherein a mass ratio of the at least one pre-bed in the at least one first reactor and the at least one main bed in the at least one second reactor is between 1:10 and 3:1.

9. The process according to claim 1, wherein the at least one main bed comprises the isomerisation catalyst and the metathesis catalyst component in a mass ratio of the isomerization catalyst to the metathesis catalyst between 5:1 and 1:1.

10. The process according to claim 1, wherein the metathesis catalyst comprises oxides of metals of the Group VIB and VIIB of the Periodic Table of Elements (PSE) deposited on at least one inorganic carrier and the at least one second catalyst component comprises oxides of metals of the Group IIA of the Periodic Table of Elements.

11. The process according to claim 1, wherein the at least one pre-bed comprises an oxide selected from the group consisting of magnesium oxide, calcium oxide, strontium oxide, barium oxide or mixtures thereof.

12. The process according to claim 1, wherein a metathesis reaction is performed in the at least one second reactor at a Weight Hourly Space Velocity (WHSV) in a range between 1 and 100 $h^{-1}$.

13. The process according to claim 1, wherein the operational temperature T1 of the at least one first reactor is at least 100° C. lower than the operational temperature T2 of the at least one second reactor.

14. The process according to claim 10, wherein the metathesis catalyst comprises oxides selected from the group consisting of tungsten oxide, molybdenum oxide, or a precursor thereof.

15. The process according to claim 10, wherein the at least one second catalyst component comprises oxides of metals of the Group IIA of the Periodic Table of Elements selected from the group consisting of magnesium oxide, calcium oxide, barium oxide, strontium oxide, or mixtures thereof.

16. The process according to claim 3, wherein the operational temperature T2 of the at least one second reactor is in a range between 290° C. and 310° C.

17. The process according to claim 6, wherein the pressure in the at least one first reactor and the at least one second reactor is between 10 to 30 bar.

* * * * *

UNITED STATES PATENT AND TRADEMARK OFFICE
CERTIFICATE OF CORRECTION

PATENT NO. : 10,202,319 B2
APPLICATION NO. : 15/021074
DATED : February 12, 2019
INVENTOR(S) : Eberhard Ernst et al.

Page 1 of 1

It is certified that error appears in the above-identified patent and that said Letters Patent is hereby corrected as shown below:

In the Claims

Column 9, Line 56, Claim 1, delete "1 butene," and insert -- 1-butene, --

Signed and Sealed this
Seventh Day of May, 2019

Andrei Iancu
*Director of the United States Patent and Trademark Office*